(12) United States Patent
Hoornaert et al.

(10) Patent No.: US 9,724,144 B2
(45) Date of Patent: Aug. 8, 2017

(54) BONE REGENERATION MEMBRANE AND METHOD FOR FORMING A BONE REGENERATION MEMBRANE

(75) Inventors: Alain Hoornaert, Nantes (FR); Pierre Layrolle, Nantes (FR); Jerome Sohier, Nantes (FR)

(73) Assignees: UNIVERSITE DE NANTES, Nantes (FR); CHU NANTES, Nantes (FR)

( * ) Notice: Subject to any disclaimer, the term of this patent is extended or adjusted under 35 U.S.C. 154(b) by 1061 days.

(21) Appl. No.: 13/809,031

(22) PCT Filed: Jul. 8, 2011

(86) PCT No.: PCT/EP2011/061704
§ 371 (c)(1),
(2), (4) Date: Jan. 8, 2013

(87) PCT Pub. No.: WO2012/004407
PCT Pub. Date: Jan. 12, 2012

(65) Prior Publication Data
US 2013/0138155 A1   May 30, 2013

(30) Foreign Application Priority Data
Jul. 9, 2010  (EP) .................................... 10305769

(51) Int. Cl.
*A61B 17/80* (2006.01)
*A61L 31/14* (2006.01)

(52) U.S. Cl.
CPC ........ *A61B 17/8085* (2013.01); *A61L 31/146* (2013.01); *A61L 31/148* (2013.01); *A61L 2400/12* (2013.01); *A61L 2430/02* (2013.01)

(58) Field of Classification Search
CPC .............. A61L 27/56; A61K 9/00; A61F 2/06
USPC .......................... 623/1.44; 435/398; 424/423
See application file for complete search history.

(56) References Cited

U.S. PATENT DOCUMENTS

| 8,911,996 B2* | 12/2014 | Srouji | A61L 27/46 435/398 |
| 2003/0100944 A1* | 5/2003 | Laksin | A61L 27/18 623/1.44 |
| 2009/0324680 A1* | 12/2009 | Reneker | A61L 31/042 424/423 |

* cited by examiner

*Primary Examiner* — Dah-Wei D Yuan
*Assistant Examiner* — Andrew Bowman
(74) *Attorney, Agent, or Firm* — Miller, Matthias & Hull LLP

(57) ABSTRACT

A bone regeneration membrane comprising:
a dense layer made of resorbable polymer, said dense layer having first and second opposite surfaces and being adapted to form a barrier to cells and soft tissues,
a nanofibrillar layer made of resorbable polymer and attached to the first surface of the dense layer, said nanofibrillar layer comprising fibers having a diameter of nanometer size, said fibers being interlaced so as to present an average pore size greater than 10 μm to allow cell permeability and bone tissue regeneration, the nanofibrillar layer having a permeability κ between $0.4*10^{-9}$ m² and $11*10^{-9}$ m², preferably between $1*10^{-9}$ m² and $4*10^{-9}$ m², in particular substantially of $2*10^{-9}$ m².

6 Claims, 9 Drawing Sheets

BONE REGENERATION MEMBRANE AND METHOD FOR FORMING A BONE REGENERATION MEMBRANE

CROSS-REFERENCE TO RELATED APPLICATIONS

This application is a U.S. national stage filing under 35 USC §371 of International Patent Application No. PCT/EP2011/061704 filed on Jul. 8, 2011, which claims priority under the Paris Convention and 35 USC §119 to the European Patent Application No. 10305769.1, filed on Jul. 9, 2010.

FIELD OF THE DISCLOSURE

The invention relates to a bone regeneration membrane and to a method for forming a bone regeneration membrane.

Although not limited thereto, the invention has a particular interest in applications in the field of odontology for dental and maxillofacial surgeries to heal bone area of a jaw.

BACKGROUND OF THE DISCLOSURE

Actually, in odontology practice, the lack of bone volume limits greatly the use of dental implants. Insufficient bone volume, both in height and thickness, may result from congenital, post traumatic, surgical procedures or may result of diseases such as periodontitis. In order to solve these clinical problems, bone augmentation materials, such as autologous bone graft, demineralised bone matrix or calcium phosphate ceramics, associated with a membrane are used prior to the implantation of dental implants. Typically, the bone augmentation material is placed in fresh alveolar bone sockets, in maxillary sinus, to augment the width or height of the alveolar crest. The bone augmentation material, as filler material (i.e. autologous bone graft, calcium phosphate ceramics), helps to regenerate bone tissue while the membrane prevents the ingrowth of fibrous tissue. After a period of healing of few months, dental implants are placed in the grafted sites. The combination of a filler material and a membrane has developed the concept of guided bone tissue regeneration (GBR).

The concept of guided bone tissue regeneration (GBR) is based on the principles of tissue healing for the bone areas. It is known since the 1980's that cells that have access and can migrate into a given wound space determine the type of tissue regenerating in this space. To apply this principle to bone augmentation, barrier membranes have been used to exclude undesired cells from the wound area (fibrous cells from the connective tissue). Concomitantly, desired cells (mesenchymal and bone cells) are favoured to migrate in the defect space. In addition to barrier function and space maintenance, it has been found useful to provide the desired cells with a defined matrix so that their migration and organisation in a new bone tissue is further enhanced.

The concept of guided tissue regeneration (GTR) is frequently applied in reconstruction of periodontal defects. Membranes are used for preventing the fast growing connective tissue to invade the defect and to allow time for periodontal ligament cementum and bone regeneration.

Although the invention has been found of particular interest in the field of odontology, the invention is not limited thereto and can find advantageous applications in other fields of guided bone tissue regeneration. For example, the invention may have advantageous applications in orthopaedic or rachis surgery.

From the known products that can be used for guided bone tissue regeneration, collageneous extracellular matrix (ECM) could provide for enhancement of the migration and the organisation of cells in a new bone tissue. But the use is hampered by lack of enough stiffness for space maintenance, low availability from allogenic sources and the possibility to transfer pathogens from xenogenic sources.

Besides, some commercially available membranes for guided tissue regeneration are made of collagen from animal origin (i.e. porcine, bovine). Examples of collagen membranes are Biogide (Geistlich Pharma AG, Switzerland), Biomend (Zimmer Dental), OsseoGuard (Biomet 3i), Inion (Inion Oy, Tempere, Finland) Guidor (Guidor AB, Huddinge, Sweden). However, these barrier membranes made of collagen carry the risk of immunological rejection and disease transfer. The biodegradation of collagen membranes in the human body is variable as depending on chemical cross linking. Furthermore, the permeability to cells and tissues is not controllable as it varies from sources.

Tissue regeneration membranes made of polymers including non resorbable polytetrafluoroethylene (PTFE, Gore-Tex, W. L. Gore & Associates inc., Elkton Md., USA) and TefGen (Lifecore Biomedical, LLC, Chaska, Minn., USA) are also known. There also exist some membranes composed of resorbable polymers, such as polylactide (PLA), polyglycolide (PGA) or a mixture thereof (PLGA). Example of resorbable polylactic membranes available on the market are Epiguide or Matrix barrier (Kensey Nash Corp). However, several problems are associated with the use of these barrier membranes. Non-resorbable membranes tend to get exposed, need a second surgery to be removed and can induce cellular reactions. Resorbable membranes overcome these drawbacks but do not provide the same quality of results, especially with regards to marginal bone gain. The cause of this discrepancy is agreed to be linked to the membrane capacity of maintaining space in the defect due to weak mechanical properties.

Current membranes exhibit poor bone regeneration capacity. To overcome these problems, bone mineral (Schwarz F, Int J Oral Maxillofac Surg 2007), calcium phosphate ceramics such as hydroxyapatite (Liao S, Biomaterials 2005), tricalcium phosphate and mixtures, calcium carbonate (Fujihara K, Biomaterials 2005), have been recently incorporated into the membranes.

Most of synthetic membranes are made in the shape of porous foam, created by traditional methods, such as particulate leaching, solvent casting or gas foaming. Recently, a new technique has been introduced, which is called electrospinning or electrostatic spinning and allows the preparation of thin fibrous membranes.

Electrospinning uses a high electric voltage of few kilovolts to draw a polymer solution or polymer melts into a whipped jet, a syringe or a capillary tube. A polymer jet is ejected from the charged polymer solution under the influence of applied electrical field. Ultrafine fibers deposit on a collector attached to the ground in the form of a non-woven structure. Fibers obtained from electrospinning exhibit diameters in the range of 50 nm to a few microns.

In order to stimulate bone formation, electrospun polycaprolactone (PCL) nano-hydroxyapatite membranes have been recently prepared (Yang F, Acta Biomaterialia 2009). Nanometer sized hydroxyapatite particles were suspended in 2,2,2-trifluoroethanol (TFE) solvent and water by ultrasonic and vigorous stirring before adding PCL polymer. Surfactant dioctyl sulfosuccinate sodium salt was dissolved in the solvent to obtain a stable particle suspension in the polymer solution. A voltage of 18-22 kV was applied to generate a polymer jet in the electro spinning set up. The resulting fibers were collected on a rotating mandrel. Previous published studies have demonstrated cell proliferation on these electrospun nanofiber membranes but not cell penetration. Furthermore, no proof of efficacy in vivo could be demonstrated with these electrospun PCL-nHA membranes.

Another membrane comprising a porous semi-permeable layer and a fibrillar layer formed by electrospinning is known from WO-A-2009/054609.

However, the known electrospun membranes do not allow suitable cell penetration or cell migration across the fibers to permit the formation of a mineralised matrix and therefore of bone tissue. The spaces between electrospun fibers are not sufficient for cell invasion. Typically, the size of a cell is around 10 μm and the space between electrospun fibers is lower than the size of a cell, thus preventing cellular invasion, cell ingrowth or cell colonization into the implantable device.

SUMMARY OF THE DISCLOSURE

The invention aims to solve one or more of the above mentioned problems.

To this end, according to a first aspect, the invention provides for a bone regeneration membrane comprising:
- a dense layer made of resorbable polymer, said dense layer having first and second opposite surfaces and being adapted to form a barrier to cells and soft tissues,
- a nanofibrillar layer made of resorbable polymer and attached to the first surface of the dense layer, said nanofibrillar layer comprising fibers having a diameter of nanometer size, said fibers being interlaced so as to present an average pore size greater than 10 μm to allow cell permeability and bone tissue regeneration, the nanofibrillar layer having a permeability κ between $0.4*10^{-9}$ m$^2$ and $11*10^{-9}$ m$^2$, preferably between $1*10^{-9}$ m$^2$ and $4*10^{-9}$ m$^2$, in particular substantially of $2*10^{-9}$ m$^2$.

Hence, the dense layer, as a support layer, prevents cellular migration from conjunctive tissues, such as gingiva in an application in odontology. Besides, while allowing the membrane to be deformed and sutured to soft tissues, the dense layer provides enough rigidity and stiffness to maintain defect space.

The nanofibrillar layer exhibits fibers with diameters in the range of collagen fibers. It is therefore a synthetic collagen as it is made of resorbable polymer. The nanofibrillar layer is an excellent support for cells allowing attachment, proliferation and differenciation at distance of several hundred microns from edges of the membrane. The nanofibrillar layer is easily degraded by hydrolysis and phagocytosis into non toxic products such as lactic acid without adverse inflammation.

Therefore, the nanofibrillar layer, as a biomimetic synthetic matrix, supports bone healing. The nanofibrillar layer of the invention has particular properties in directing cellular repair and tissue regeneration processes. The nanofibrillar layer provides the cells with a structure similar to native collagen networks in its organization and properties. The obtained fiber matrix have high surface to volume ratios and high porosity, with pore size greater than the average cell size (e.g. 10 μm) and an appropriate permeability which cannot be obtained by electrospun membranes, to allow cell migration across the membrane towards the bone defect to be repaired. The invention improves greatly the guided bone regeneration approach for bone augmentation by combining the functions of barrier, space maintenance and bone formation.

Besides, according to the invention, both layers are made of resorbable polymers, these resorbable polymers being the same or different, thus rendering the whole membrane biodegradable and resorbable to improve its biocompatibility and its implantability, and the safety of a patient to whom the membrane is implanted.

The permeability κ is calculated by the equation:

$$\kappa = \Delta Q * L * \mu / (\Delta P * A)$$

where,
ΔQ is a flow rate of liquid through a sample of nanofibrillar layer, said flow rate being determined by the measure of a volume of liquid passing though the sample of nanofibrillar layer and collected during a determined time interval (m$^3$/s),
L is a length of the sample of nanofibrillar layer (m),
μ is a kinematic fluid viscosity of the liquid (Pa*s),
ΔP is the pressure drop across the sample of nanofibrillar layer determined by the difference between the pressures on opposite surfaces of the sample of nanofibrillar layer (Pa), and
A is a cross-sectional area of the sample of nanofibrillar layer (m$^2$).

The nanofibrillar layer may have a porosity $p_{nl}$ greater than 90%, preferably substantially of 95%. Such porosity $p_{nl}$ is calculated by the equation:

$$p_{nl} = 1 - (W_{snl} / (V_{snl} * d_{polymer\ nl}))$$

where,
$W_{snl}$ is the weight of a sample of nanofibrillar layer,
$V_{snl}$ is the volume of the sample of nanofibrillar layer,
$d_{polymer\ nl}$ the density of the polymer of which the nanofibrillar layer is made.

By contrast with the nanofibrillar layer, the dense layer may be a substantially non-porous film. In particular, the dense layer may have a porosity $p_{dl}$ less than 10%, preferably less than 5%. Such porosity $p_{dl}$ is calculated by the equation:

$$p_{dl} = 1 - (W_{sdl} / (V_{sdl} * d_{polymer\ dl} d_{polymer\ dl}))$$

where,
$W_{sdl}$ is the weight of a sample of dense layer,
$V_{sdl}$ is the volume of the sample of dense layer,
$d_{polymer\ dl}$ is the density of the polymer of which the dense layer is made.

The dense layer and the nanofibrillar layer may be attached to one another by hydrogen bonds.

The dense layer may have a thickness comprised between 30 μm and 70 μm, preferably between 45 μm and 55 μm, and the nanofibrillar layer has a thickness comprised between 200 μm and 300 μm, preferably between 230 μm and 270 μm.

The nanofibrillar layer may be composite and incorporate particles adapted to support bone formation, said particles being distributed between the fibers. In particular, the particles may be calcium phosphate particles.

The addition of these particles into the nanofibrillar layer ensures a scaffold for bone tissue formation. As the fibers of the nanofibrillar layer degrade, particles serve as substrate for bone cells and are osteoconductive.

According to a second aspect, the invention provides for a method for forming a bone regeneration membrane, comprising the steps of:

forming, at room temperature, a dense layer made of resorbable polymer, said dense layer having first and second opposite surfaces and being adapted to form a barrier to cells and soft tissues, forming, at room temperature, a nanofibrillar layer made of resorbable polymer, said nanofibrillar layer comprising fibers having a diameter of nanometer size, the step of forming the nanofibrillar layer comprising the steps of:

mixing the resorbable polymer with a solvent to obtain a polymer solution, feeding a spray nozzle with said polymer solution, projecting said polymer solution through said nozzle with a gas jet adapted to pump the polymer solution by depression, wherein the projected resorbable polymer precipitates and solidifies by evaporation of the solvent to form the fibers interlaced so as to present an average pore size greater than 10 µm to allow cell permeability and bone tissue regeneration, the nanofibrillar layer (3) having a permeability κ between $0.4*10^{-9}$ $m^2$ and $11*10^{-9}$ $m^2$, preferably between $1*10^{-9}$ $m^2$ and $4*10^{-9}$ $m^2$, in particular substantially of $2*10^{-9}$ $m^2$, depositing the fibers on a collecting surface, attaching, at room temperature, said nanofibrillar layer to the first surface of the dense layer.

The invention provides for a simple method to obtain nanometer sized fibers presenting a suitable structure of a biomimetic synthetic matrix that promotes the directing of cellular repair, the tissue regeneration processes and thereby the bone healing. Conversely to the methods for forming the known membranes, the method of the invention is efficient and scalable, thanks to the reproducibility it provides. Besides with the method of the invention, the diameter and distribution of nanometer fibers can easily be controlled by parameters such as polymer concentration, gas jet pressure, aperture of nozzle, spraying distance, etc. Besides, by contrast with electrospinning, the method is safe since it does not require high voltage. Besides, conversely to known methods, the method of the invention is implemented at room temperature, generally 20° C. to 25° C.

The dense layer may be formed by film casting. The step of forming the dense layer may then comprise the steps of:

mixing the resorbable polymer with a solvent to obtain a polymer solution, casting said polymer solution onto a collecting surface, spreading said polymer solution on the collecting surface, wherein the cast and spread resorbable polymer precipitates and solidifies by evaporation of the solvent to form a substantially non-porous film.

In one embodiment, the nanofibrillar layer is deposited on the first surface of the dense layer as collecting surface during the step of spreading the polymer solution, the step of attaching the nanofibrillar layer to the first surface of the dense layer comprising the formation of hydrogen bonds as the polymer of which the dense layer is made precipitates and solidifies by evaporation of the solvent. The formation of hydrogen bonds ensures a good bonding strength between the dense layer and the nanofibrillar layer.

In another embodiment, at the step of projecting the polymer solution, the polymer solution is directly projected onto the first surface of the dense layer, and at the step of depositing the fibers, the fibers are directly deposited on the first surface of the dense layer as collecting surface, the step of attaching the nanofibrillar layer to the first surface of the dense layer comprising the formation of hydrogen bonds as the polymer of which the nanofibrillar layer is made precipitates and solidifies by evaporation of the solvent.

The step of forming a nanofibrillar layer may further comprise, at the step of projecting the polymer solution, spraying particles adapted to support bone formation.

The method may further comprise a step of sterilising the bone regeneration membrane.

BRIEF DESCRIPTION OF THE DRAWINGS

Other objects and advantages of the invention will emerge from the following disclosure of particular embodiments given as non limitative example, made in reference to the enclosed drawings in which:

FIGS. 7a and 7b are cross-section microscopic views of a representative calvaria defect covered during four weeks by the bi-layered bone regeneration membrane of FIG. 1, FIG. 7a being a section of the first third of the defect while FIG. 7b is a section of the middle of the defect, FIGS. 10a and 10b are cross section microscopic views of a representative calvaria defect covered during four weeks by a commercial PLA dense membrane, FIG. 10a being a section of the first third of the defect while FIG. 10b is a section of the middle of the defect.

DETAILED DESCRIPTION

On the Figures, the same reference numbers refer to the same or similar elements.

Figure 1:
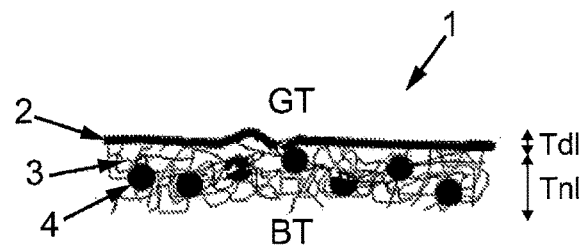
FIG. 1 is a schematic view of a bi-layered bone regeneration membrane according to an embodiment of the invention, the bone regeneration membrane comprising a dense layer and a nanofibrillar layer.
Figure 2A:
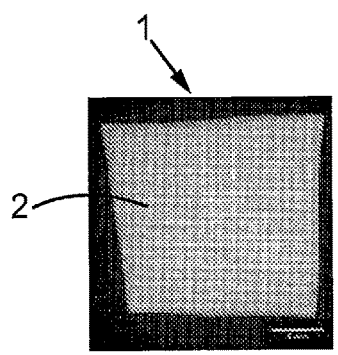
FIGS. 2a and 2b are respectively a macroscopic view of a surface of the dense layer opposite to the nanofibrillar layer and a macroscopic cross-section view of the bone regeneration membrane of FIG. 1, FIGS. 3a and 3b are respectively microscopic views of the dense layer and the nanofibrillar layer of the bone regeneration membrane of FIG. 1.
Figure 2B:
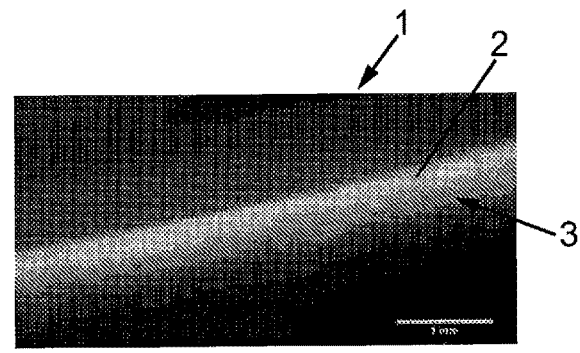

FIGS. 1, 2a and 2b represent a biocompatible and implantable bone regeneration membrane 1 suitable for repairing a bone defect within the body of a patient.

The membrane 1 is substantially flat with a thickness comprised between 50 µm and 2500 µm, and is further able to be deformed and/or cut so as to enable a surgeon placing the membrane on the bone defect to shape the membrane 1 in any appropriate manner. The illustrated membrane presents a polygonal, for example square, contour. However, depending on the application, the membrane of suitable dimensions may have any other contour, such as rectangular, circular, elliptic or other.

The bone regeneration membrane 1 comprises:
- a dense layer 2 forming a support layer which forms a barrier to cells and soft tissues in order to prevent cellular migration from conjunctive tissues, and which provides for enough rigidity and stiffness to maintain a space of the defect to be repaired,
- a nanofibrillar layer 3 forming a biomimetic synthetic matrix which provides the mesenchymal and bone cells with a structure similar to native collagen networks in its organization and properties to allow mesenchymal and bone cell penetration, migration and differentiation into osteoblasts, and to thereby promote bone healing.

Both the dense layer 2 and the nanofibrillar layer 3 are composed of well known biodegradable and resorbable polymers, such as polycaprolactone, polylactic acid, polyglycolic acid, polycarbonate and mixtures thereof. The resorbable polymers for the dense layer 2 and the nanofibrillar layer 3 may be the same or two different polymers.

Figure 3A:
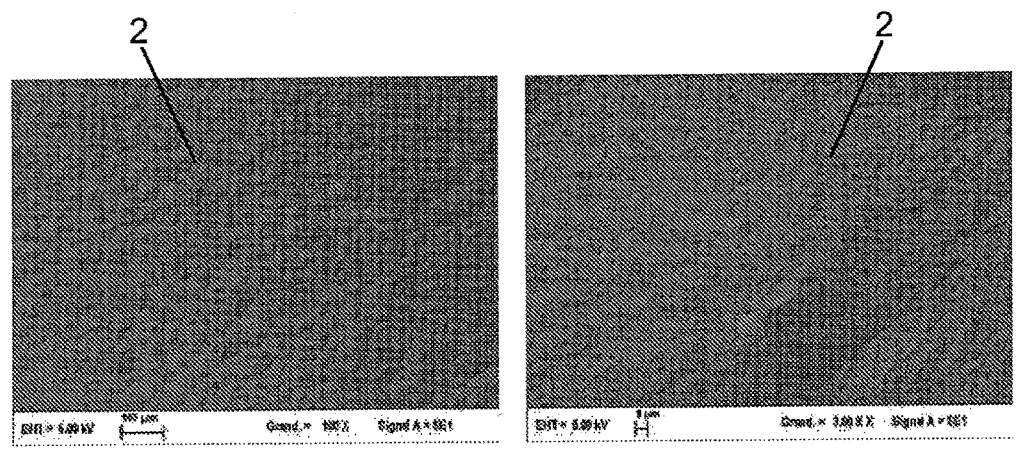
FIG. 3c is an enlarged microscopic view of the nanofibrillar layer showing fibres of nanometer size and calcium phosphate particles interlaced therebetween.

The dense layer 2, of which a microscopic view is visible on FIG. 3a, is a continuous, substantially non-porous film having first and second surfaces extending respectively on opposite first and second faces. In the illustrated embodiment, the dense layer 2 has a thickness $T_{dl}$ comprised between 20 µm and 500 µm, preferably between 30 µm and 70 µm, more preferably between 45 µm and 55 µm.

As regards to the porosity, the dense layer 2 said to be substantially non-porous has a porosity $p_{dl}$ less than 10%, preferably less than 5%, the porosity $p_{dl}$ being calculated by the equation:

$$p_{dl}=1-(W_{sdl}-(V_{sdl}*d_{polymer\ dl}))$$

where,
$W_{sdl}$ is the weight of a sample of dense layer,
$V_{sdl}$ is the volume of the sample of dense layer,
$d_{polymer\ dl}$ is the density of the polymer of which the dense layer is made.

Such dense layer 2 may be made by film casting at room temperature.

To do so, in a first step, a polymer solution is prepared by dissolving the resorbable polymer in an appropriate organic solvent, such as chloroform, so as to obtain a liquid mixture. Then, in a subsequent step, the polymer solution is cast onto a collecting surface formed for example on a plate made of glass or of Teflon, the polymer solution being then spread on the collection surface by a film casting applicator to form a film. At this step, the thickness of the film is set between 100 µm and 400 µm. The film is dried, for example placed beneath a hood, so that the solvent may evaporate and the resorbable polymer may precipitate and solidify.

The nanofibrillar layer 3 is attached to the first surface of the dense layer 2. As can be seen on FIG. 3b, the nanofibrillar layer 3 comprises fibers having a diameter of nanometer size, for example between 100 nm and 1 µm, especially between 300 µm and 800 µm. The nanofibrillar layer has a thickness $T_{nl}$ between 30 µm and 2000 µm, preferably between 100 to 500 µm, more preferably between 200 µm and 300 µm, especially between 230 µm and 270 µm.

To allow the mesenchymal and bone cells, such as fibroblasts, having an average diameter between 5 µm and 10 µm, to penetrate and migrate within the nanofibrillar layer 3, the nanofibrillar layer 3 presents an open network formed of interlaced fibers and presenting an average pore size greater than 10 µm.

Permeability of the resulting nanofibrillar layer 3 can be evaluated using a method that applies Darcy's law (M J Grimm, J L Williams. "Measurements of permeability in human calcaneal trabecular bone". Journal of Biomechanics 1997; 7: 743-5; P W Hui, P C Leung, A Sher. "Fluid conductance of cancellous bone graft as a predictor for graft-host interface healing". Journal of Biomechanics 1996; 1: 123-32).

A liquid is forced through a sample of nanofibrillar layer by applying a constant pressure. From the induced flow rate, the fluid conductance C can be evaluated as follows:

$$C=\Delta Q/\Delta P$$

where,
$\Delta Q$ is a flow rate of liquid through a sample of nanofibrillar layer, said flow rate being determined by the measure of a volume of liquid passing though the sample of nanofibrillar layer and collected during a determined time interval (m$^3$/s), and
$\Delta P$ is the pressure drop across the sample of nanofibrillar layer determined by the difference between the pressures on opposite surfaces of the sample of nanofibrillar layer (Pa).

Applying Darcy's law to the porous sample of nanofibrillar layer, the conductance C can be obtained as:

$$C=A*\kappa/(L*\mu)$$

where
A is a cross-sectional area of the sample of nanofibrillar layer (m$^2$),
$\kappa$ is the permeability of the nanofibrillar layer (m$^2$),
L is a length of the sample of nanofibrillar layer (mm),
$\mu$ is a kinematic fluid viscosity of the liquid (Pa*s).

Thus, the permeability $\kappa$ can be calculated by the equation:

$$\kappa=\Delta Q*L*\mu/(\Delta P*A).$$

The permeability can be used to compare the pore interconnectivity of different structures.

Advantageously, the nanofibrillar layer has a permeability $\kappa$ within the same range as that of the trabecular bone, i.e. between $0.4*10^{-9}$ m$^2$ and $11*10^{-9}$ m$^2$.

Figure 11A:
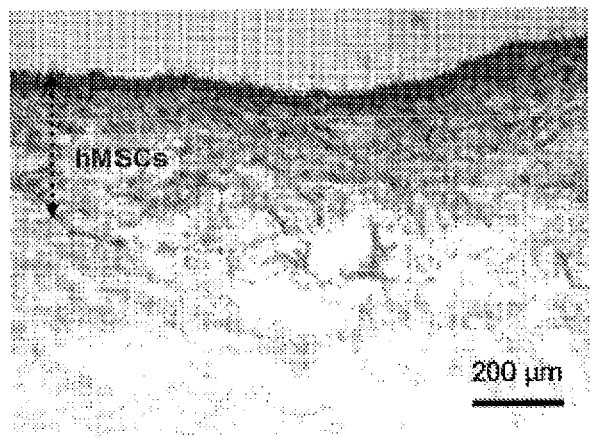
FIGS. 11a and 11b illustrate histology cryo sections of nanofiber polylactic glycolic acid membrane after respectively eleven and twenty-one days of culture of human mesenchymal stem cells.
Figure 11B:
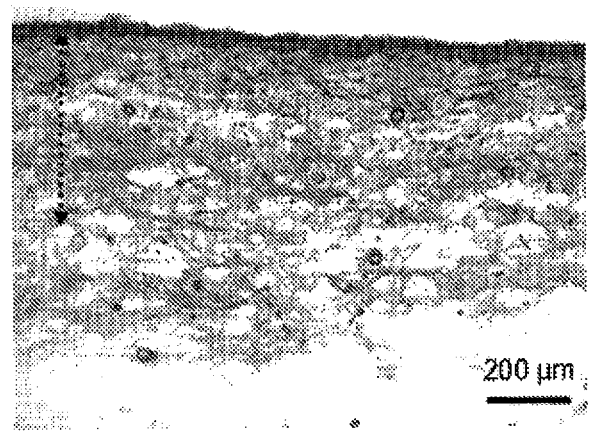

An illustration of the permeability of the nanofibrillar layer to cells is shown as an example on FIGS. 11a and 11b which illustrate histology cryo sections of nanofiber polylactic glycolic acid membrane after respectively eleven and twenty-one days of culture of human mesenchymal stem cells. The membrane was of 1 cm$^2$×1 mm thickness and the mean diameter of nanofibers was 600 nm, the cell seeding density being 10$^6$ hMSC. The size of cells is approximately 10 µm. In this example, human mesenchymal stem cells from bonemarrow have been seeded onto the membrane. After 11 and 21 days of culture, methylene blue staining clearly indicates cell growth and cell permeability into the membrane. Therefore, this example illustrates that the spaces between nanofibers are sufficiently wide to allow cell ingrowth and thus greater than 10 µm.

The nanofibrillar layer 3 is much less dense than the dense layer 2 and presents, in this respect, a porosity $p_{nl}$ greater than 90%, preferably substantially of 95%. As for the dense layer 2, the porosity $p_{nl}$ of the nanofibrillar layer can be calculated by the equation:

$$p_{nl}=1-(W_{snl}-(V_{snl}*d_{polymer\ nl}))$$

where,
$W_{snl}$ is the weight of a sample of nanofibrillar layer,
$V_{snl}$ is the volume of the sample of nanofibrillar layer,
$d_{polymer\ nl}$ is the density of the polymer of which the nanofibrillar layer is made.

Figure 3B:
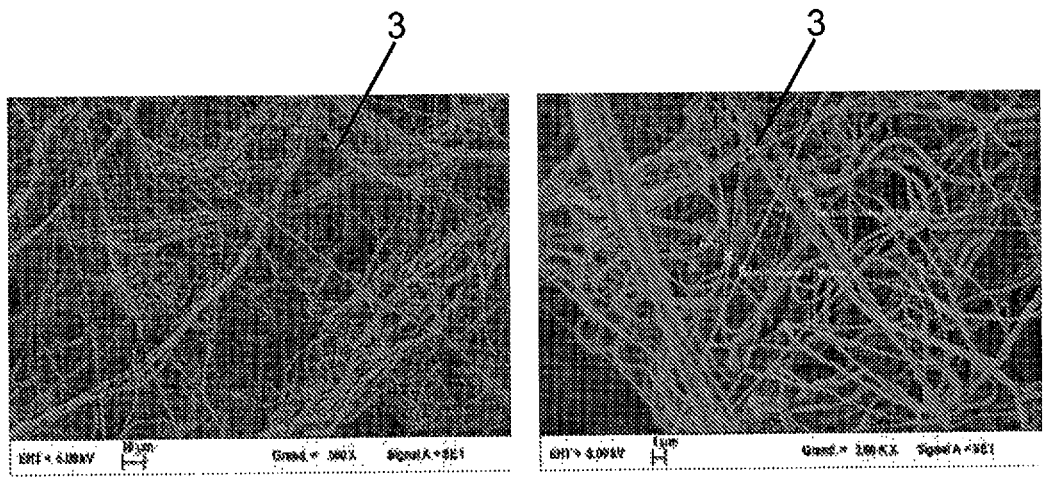
Figure 3C:
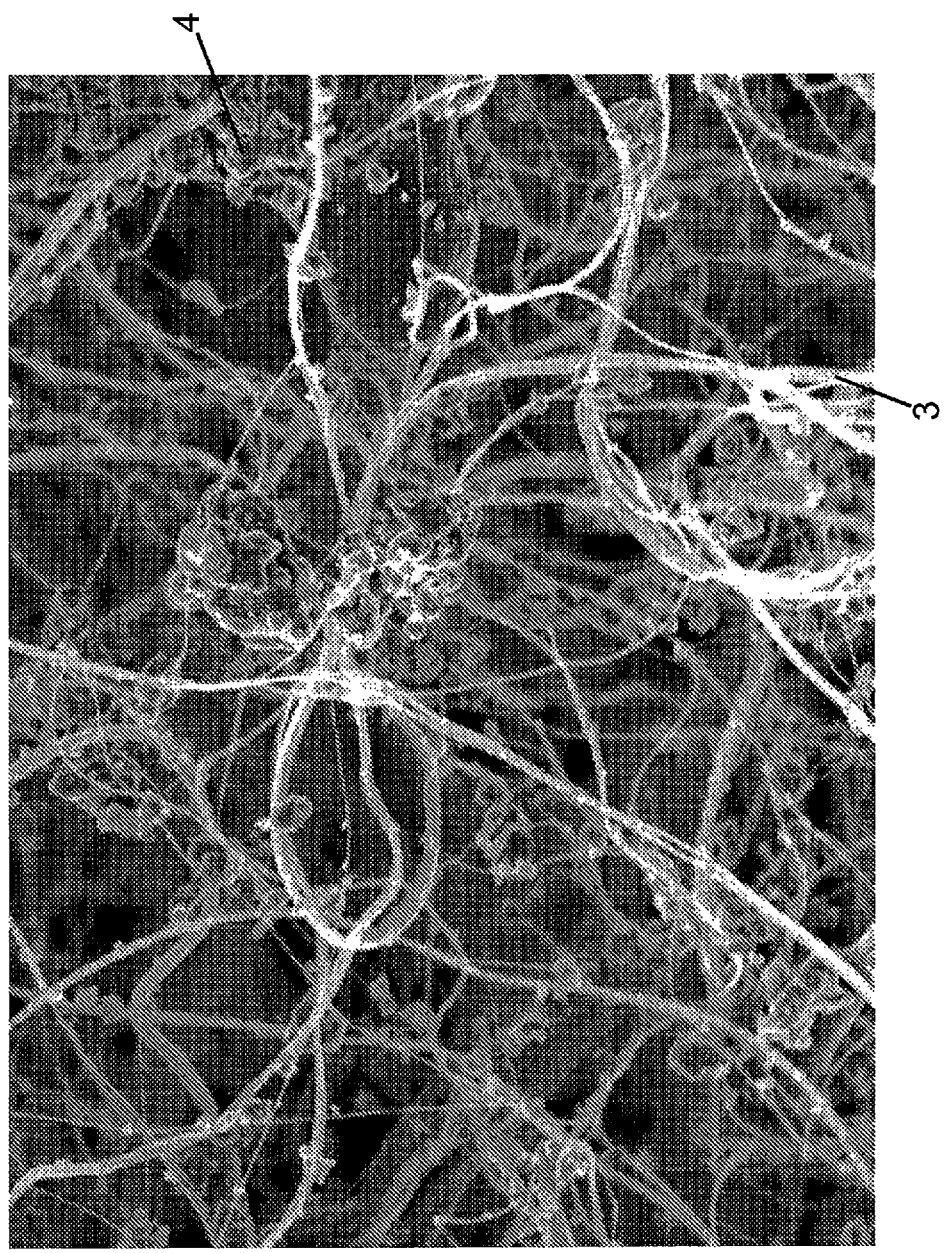

In the illustrated example, as illustrated on FIG. 3c, the nanofibrillar layer 3 is composite and comprises, in addition to the fibers, particles 4 adapted to support bone formation distributed between the fibers.

In a particular example, the particles 4 are calcium phosphate particles comprising beta-tricalcium phosphate, hydroxyapatite, carbonate apatite or mixtures thereof. The size of calcium phosphate particles should be in the range form 50 µm to 1000 µm, preferably from 100 µm to 200 µm. The particles 4 are preferably spherical to facilitate free flowing in air, as it will become apparent from the following of the description.

Besides, the nanofibrillar layer 3 may further comprise biological active compounds such as growth factors, antibiotics or others incorporated between the fibers.

Figure 4:
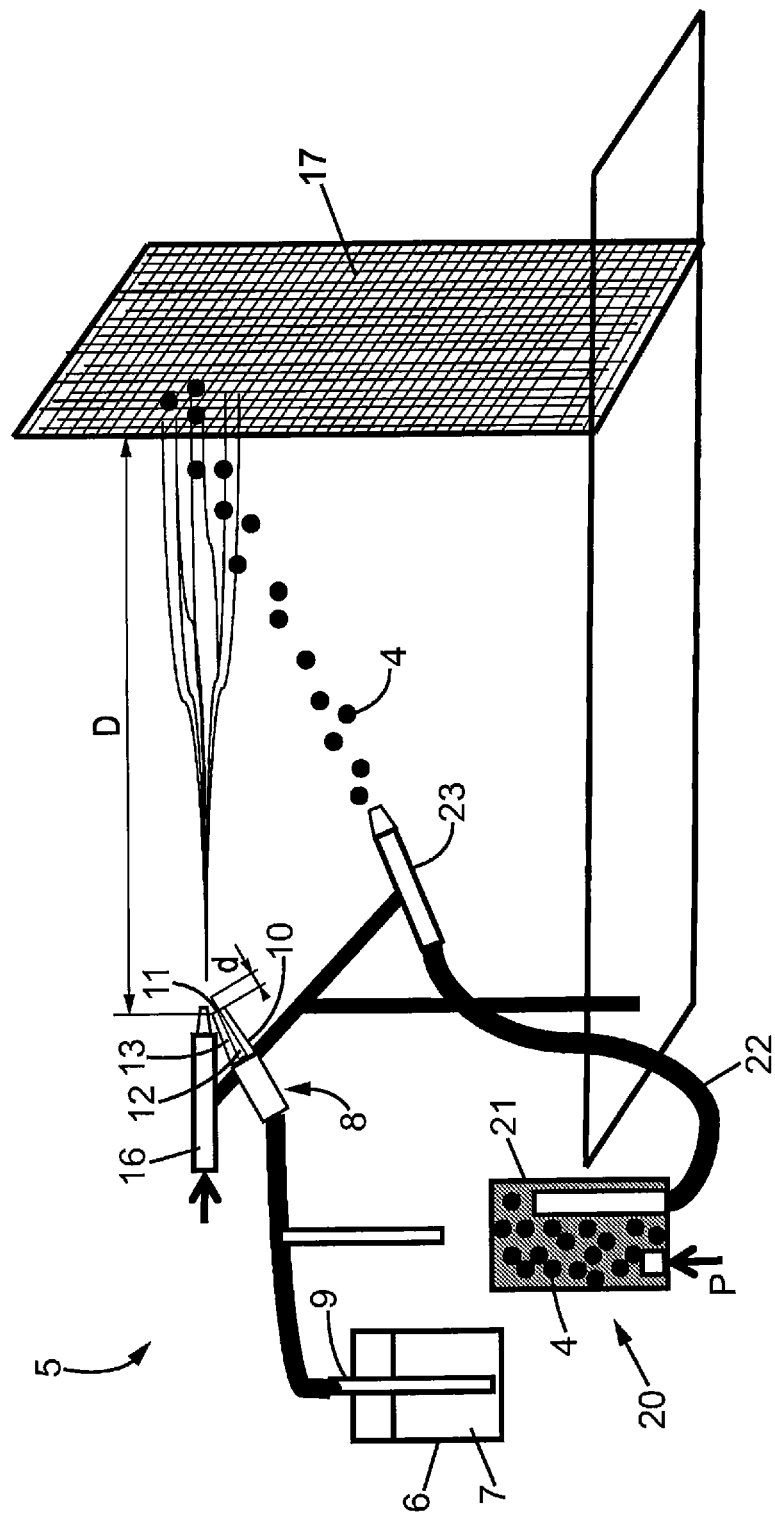
FIG. 4 is a schematic view of a device for forming the nanofibrillar layer of the bone regeneration membrane of FIG. 1.

In reference to FIG. 4, a device 5 for manufacturing the nanofibrillar layer 3 is disclosed.

The device 5 comprises a container 6 which contains a polymer solution 7 obtained by mixing the resorbable polymer of which the nanofibrillar layer is made with an organic solvent, such as chloroform. The container 6 is connected to a nozzle 8 though a pipe 9 so that polymer solution 7 may be supplied to the nozzle 8.

The nozzle 8 comprises an outer conical tube 10 extending along a longitudinal axis and having an outlet orifice 11. A center conical needle 12 is movable along the longitudinal axis of the tube 10. A passageway 13 is defined between the outer tube 10 and the needle 12. The polymer solution may then be transferred toward the outlet orifice 11 through the passageway 13. The conical aspect of the outer tube 10 and the needle 12 is such that the needle 12, by moving longitudinally, adjusts the size of the outlet orifice 11.

The outlet orifice size may be defined by the distance d between the needle tip and the outer tube end, where d is positive, by convention, when the needle summit is inside the outer tube 10.

A tube 16 conducts a gas jet, typically compressed air at a pressure of 3 bars to 6 bars, towards the external of the outlet orifice 11. Although other configuration are possible, in the illustrated embodiment, the tube 16 and the nozzle 8 form an acute angle such that the gas jet creates a depression at the outlet orifice 11. By creating the depression, the gas jet pumps the polymer solution from the container 6 to the nozzle 8 where it is diffracted by the cooperation of the outer tube 10 with the needle 12 and projected onto a collecting surface 17 disposed at a distance D from the outlet orifice 11.

In the illustrated embodiment, the device 5 further comprises an air spraying device 20 for projecting the calcium phosphate particles 4 onto the collecting surface 17. The calcium phosphate particles 4 are suspended by air pressure P, shown by an arrow, into a container 21. A tube 22 adapted to transport the calcium phosphate particles 4 therethrough extends from the container 21 to a nozzle 23 through which the calcium phosphate particles 4 are projected to the collecting surface 17. Both nozzles for polymer solution 7 and calcium phosphate particles 4 are arranged so as to be directed to the same point in the collecting surface 17.

Figure 5:
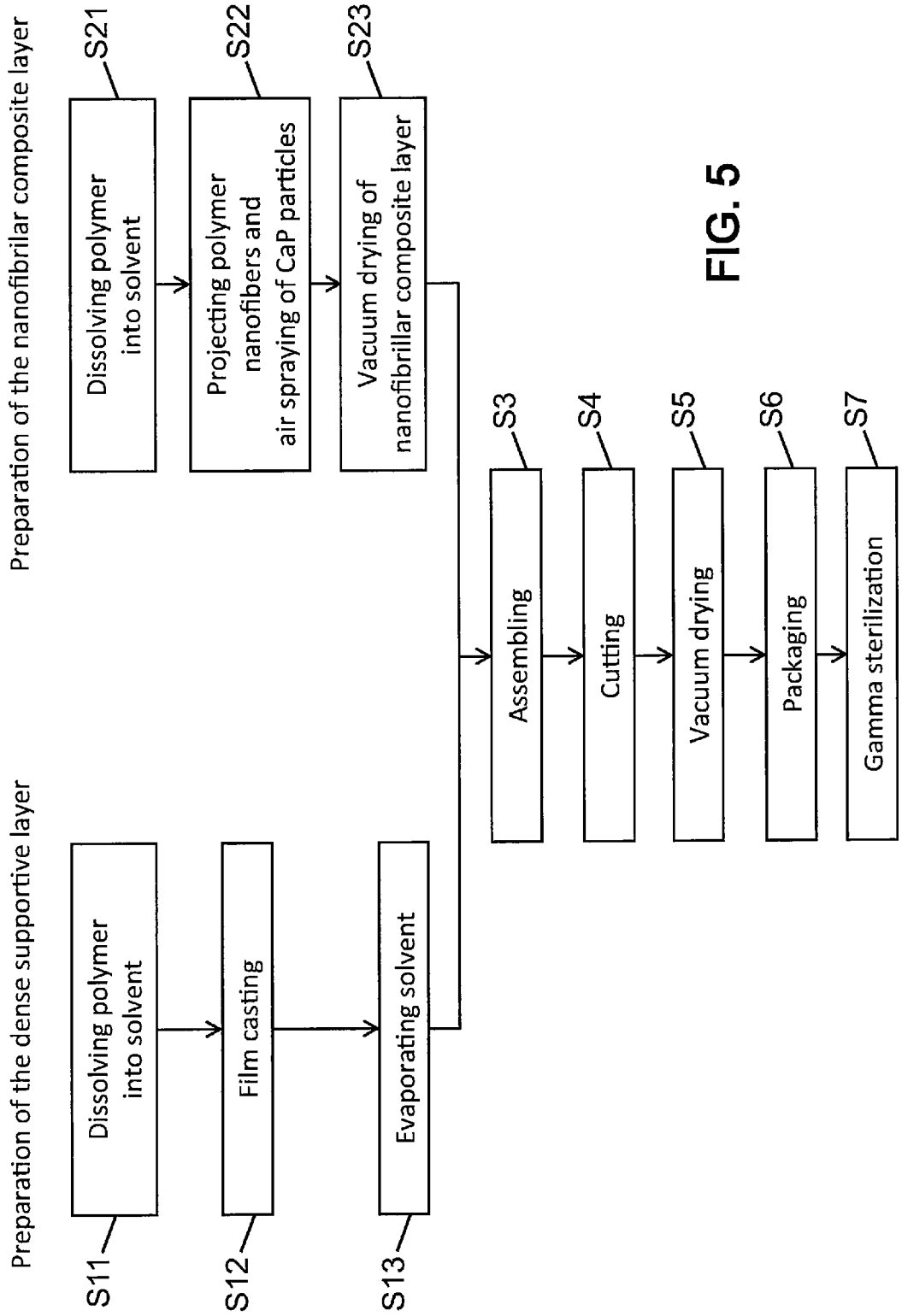
FIG. 5 is a flowchart illustrating the steps of a method for forming the bone regeneration membrane of FIG. 1.

A method for forming the above disclosed bone regeneration membrane 1 is now disclosed in relation to the flowchart illustrated on FIG. 5.

As can be seen on the left part of the flowchart, the dense layer 2 has been prepared by film casting as previously disclosed with the steps:
S11 wherein the resorbable polymer of which the dense layer 2 is made is dissolved in the solvent to obtain the polymer solution,
S12 wherein the polymer solution is cast and spread onto the collecting surface,
S13 wherein the solvent evaporates and the resorbable polymer precipitates and solidifies.

A method for preparing nanofibrillar layer 3 implementing the above disclosed device 5 is represented on the right part of the flowchart of FIG. 5.

At a first step S21, the polymer solution 7 is prepared by dissolving the resorbable polymer with the appropriate solvent, e.g. chloroform. In a particular embodiment, the biological active compounds such as growth factors, antibiotics or others may be introduced at that step in the polymer solution.

At a subsequent step S22, at room temperature, an air flow is applied within the tube 16 so as to create a depression at the outlet orifice 11 of the nozzle 8 that pumps the polymer solution from the reservoir 6 and through the pipe 9 to feed the nozzle 8 and project a jet of polymer solution from the outlet orifice 11 of the nozzle 8. The biological active compounds are projected at the same time, at room temperature, together with the polymer solution. The projection of the polymer solution by the air flow causes a quick evaporation of a part of the solvent and thereby initiates the precipitation of the polymer solution in fibers of nanometer size.

As shown of FIG. 5, at step S22, concomitantly to the step of projecting the polymer solution, the calcium phosphate particles 4 can be sprayed towards the first surface of the dense layer 2 from a container where air is introduced to create a venturi. The dispersion of particles 4 in air is sprayed together with the polymer solution. Calcium phosphate particles 4 are held by the fibers as the polymer is dried.

The calcium phosphate particles 4 are projected simultaneously with the polymer solution 7 by using the air spraying device. Both spray nozzles for polymer solution 7 and calcium phosphate particles 4 are aligned to the same point in the collecting surface 17. The calcium phosphate particles 4 are suspended by air pressure into the container 21, transported through the tube 22 and projected to the collecting surface 17 through the nozzle 23.

At step S23, the polymer solution is then dried for example through vacuum drying to evaporate the remaining solvent and to obtain the nanofibrillar layer. As the nanometer sized fibers solidify by solvent evaporation, calcium phosphate particles 4 are entrapped into the interlaced fibers.

In an embodiment, the collecting surface 17 may be the first surface of the dense layer 2 onto which the polymer solution is directly projected. In this case, the fibers are directly deposited on the first surface of the dense layer 2. The presence of residual solvent allows the fibers to form hydrogen bonds that solidly attach the fibers to each other and to the first surface of the dense layer 2 as the residual solvent evaporates and the polymer of which the nanofibrillar layer is made precipitates and solidifies. This provides for a membrane having improved bonding strength and resistance to torsion and elongation. In this case, the step S3 of attaching the nanofibrillar layer 3 to the dense layer 2 is performed at the same time as the step S23 of drying the nanofibrillar layer 3.

In a variant, instead of projecting the polymer solution intended to form the nanofibrillar layer and, where appropriate, of spraying the particles 4 directly onto the dense layer 2, the polymer solution and possibly the particles 4 are projected onto a separate collecting surface 17. The nanofibrillar layer 3 is thereby formed apart from the dense layer 2.

At the step S12 of spreading the polymer solution intended to form the dense layer 2 on the collecting surface, the nanofibrillar layer 3 may be placed in contact to the first surface of the dense layer 2 containing residual solvent. A roller may be applied to air bubbles between the dense layer 2 and the nanofibrillar layer 3. As the dense layer 2 is dried, the solvent evaporates and the polymer of which the dense layer 2 is made precipitates and solidifies. Hydrogen bonds are formed between the nanofibrillar layer 3 and the dense layer 2 providing for a strong attachment of the nanofibrillar layer 3 to the first surface of the dense layer 2. In this case, the step S3 of attaching the nanofibrillar layer 3 to the dense layer 2 is performed at the same time as the step S12 of film casting and spreading the polymer solution of the dense layer.

The invention is not limited to the above disclosed steps S3 of attaching the dense layer and the nanofibrillar layer. These layers can be attached to each other in any suitable manner after having been formed separately as illustrated on FIG. 5.

The resulting bi-layered bone regeneration membrane may then be cut to the desired shape and dimension (step S4) and vacuum dried (step S5) if necessary. The bone regeneration membrane may then be sterilized (step S7), for example by gamma irradiation, possibly after having been packaged (step S6).

Although not limited thereto, the bone regeneration membrane is suitable for use in odontology for dental and maxillofacial surgeries.

In post-extraction surgery, the membrane may be used to isolate the dental alveolus after the extraction, ease hemostasis and sutures and promote bone growth while maintaining the volumes of the internal and external alveolar tables.

In periodontal surgery, the membrane can be used to fill periodontal bone lesions after treatment of the focus of infection.

In implanting surgery, for pre-implanting surgery, during sinus grafts, the bone regeneration membrane may be placed to obturate the membrane of Schneider or to protect it from the physical stress of biomaterials. The bone regeneration membrane may also be placed to obturate the bone opening on the lateral wall of the sinus. In the Summers's technique, the bone regeneration membrane may be placed at the apex of the implant to isolate the membrane from the sinus et promote the apparition of bone cortical.

During the correction of bone defects, the membrane may be used to cover biomaterials filling an alveolar defect, to cover and isolate apposition autograft or to isolate and regenerate sampling locations.

During the placement of implants, the membrane may be used to cover exposed threads in the occurrence of bone dehiscence or fenestration during the surgery.

As can be seen on FIG. 1, the device is easily implanted in dental defects with the dense layer 2 in contact to gingival tissue GT and the composite nanofibrillar layer 3 in contact to bone tissue BT. The implantable membrane is sutured to connective tissue and held with pins into bone or fixed with medical glue.

After implantation, the composite nanofibrillar layer stimulates human mesenchymal and bone cell migration in the defect and the production of mineralized collagen.

Depending on polymer composition and molecular weight, different degradation times are obtained. The optimal degradation time should match the rate of bone tissue formation. The polymers of which the dense layer 2 and the nanofibrillar layer 3 are made are degraded by hydrolysis, and resulting fragments are degraded by phagocytosis by macrophage cells. In particular, the nanofibrillar layer is rapidly degraded by phagocytosis. The hydrolysis of the nanofibrillar layer is also rapider thanks to its porosity and its exchange surface with the body fluids. As the fibers of the nanofibrillar layer are degraded, calcium phosphate particles 4 support bone tissue growth by osteoconduction.

Figure 6:
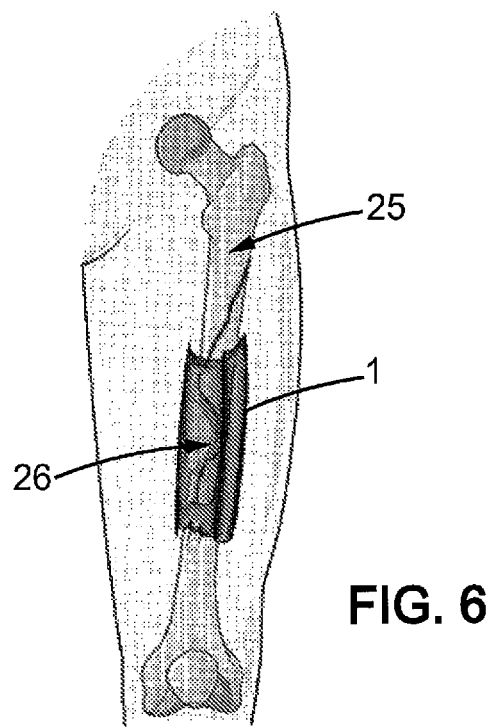
FIG. 6 is a representation of the implementation of the bone regeneration membrane of the invention in orthopaedic surgery for healing a bone fracture.

However, the invention may also find an interest in other applications such as orthopaedic surgery. In this respect, FIG. 6 illustrates a bone regeneration membrane 1 sized and shaped for healing a bone fracture 26 of femur 25. The bone regeneration membrane 1 is wrapped around the fracture 26 of femur 25 with the nanofibrillar layer 3 directed towards the femur 25.

Examples

Materials

Bi-Layered Membrane

Poly (ε-Carpolactone) (PCL, molecular weight 80000 g/mol) and poly DL-lactide/glycolide copolymer (PLGA, 50/50 molar ratio, inherent viscosity 0.4 dl/g) were respectively purchased from Solvay Caprolactones (Warrington, United Kingdoms) and Purac biomaterials (Gorinchem, The Netherlands). Analytical grade chloroform was obtained from MP Biochemicals (Eschwege, Germany). Glycol methacrylate and formaldehyde were acquired from Sigma Chem. corp. (St. Louis, United States of America). These chemicals were used as received. The projection system was based on the above disclosed method and device.

The nanofibrillar layer was produced according to the above disclosed method. PCL or PLGA were dissolved in chloroform at a concentration of respectively 0.1033 g/ml and 0.25 g/ml. The solution was sprayed on a metallic grid distant of 30.65 cm using an air pressure of 7 bars. The spraying opening for PCL was of −0.54 mm and of −0.64 mm for PLGA. Two successive sprayings of 1 minute were performed to create the layer, which was subsequently removed from the grid.

Tricalcium phosphate particles are produced by precipitation from calcium and phosphate solutions at pH 9-10. The particles are sprayed, air dried and sintered at 1050° C. for 5 hours. The particles are sieved between 100 μm to 200 μm and are spherical in shape. Particles are placed in a grit blasting apparatus and sprayed with air pressure of 6 bars. At the same time, nanofibers are deposited from a polymer solution using an air pressure of 7 bars as previously described. The nanofibers hold calcium phosphate particles forming a composite non woven mesh. The mineral content in the composite nanofiber layer is comprised between 10 wt. % to 70 wt. %.

A dense PCL film was created from using a film casting applicator. A PCL solution in chloroform (0.1033 g/ml) was deposited on a glass plate and processed with the film applicator set at a thickness of 100 μm. The film was let to evaporate slowly under fumehood and the level of evaporation assessed visually every 5 minutes.

Once solvent evaporation was almost complete, the PCL cast film was covered by the biomimetic nanofibrillar layer. The complete membranes were then left under fumehood until full solvent evaporation. After being removed from the glass plate, the bi-layered membranes were placed in a vacuum dessicator overnight.

General morphology of each membrane layer was investigated using a scanning electron microscope (SEM, Leo 1450VP, Karl Zeiss SMT, Oberkochen, Germany). All samples were gold sputtered prior to observation (Desk III, Denton vacuum, Moorestown, USA). The fiber diameters and distribution of nanofibrillar layers were measured with a specifically designed program based on the quantimet Q550 image analysis software (Leica, Wetzlar, Germany). After thresholding the SEM images, the software detected the longitudinal axis of each fiber and computed fiber diameter from vectors drawn perpendicular to that axis. For each sample, nine SEM pictures, taken randomly at three different magnifications (1000, 2500, 5000×), were analyzed. For each fiber, three diameters were selected along the fiber and on average around 460 values were obtained for each jet-sprayed sample. From these data, average diameter and distribution were computed for each sample and the intercentile distances 1-99% was used to characterize the range of fiber distribution.

Size and thickness of membranes and individual layers was measured using a caliper at three different locations.

Membrane density (mg/cm$^2$) was obtained by weighting a 1 cm*1 cm membrane while the average porosity (%) of the nanofibrillar layers was evaluated from the dry weight and dry volume of cylindrical samples of nanofibrillar layers (12 mm in diameter and variable thicknesses).

Permeability of the nanofibrillar layers was evaluated as described above using pure water forced through the nanofibrillar layers by applying a constant pressure. The flow rate is measured, from which the value of the permeability can be deducted. Cylindrical samples of nanofibrillar layers (12 mm in diameter and variable thicknesses) were placed between 2 polystyrene tube (8 mm inner diameter and 30 mm long) and tightly sealed by wrapping parafilm around the tubes interface. The polystyrene tubes were then connected to a reservoir of demineralized water by a rubber tube (inner diameter 10 mm). The difference in water level between the reservoir and the sample corresponded to 0.58 m. Assuming that the pressure at the bottom surface of the samples equals zero, the pressure generated by the water level was 5.69 kPa. To keep the pressure difference approximately constant during the experiment, the flow volume was restricted at 100 ml. A volume of 100 ml would have reduced the water level in the reservoir by 7.1 mm, corresponding to a negligible 0.5% pressure drop. The induced flow was deducted from the volume of water collected during a certain time interval.

Rabbit Calvaria Defect

Animals

This study has been approved by the Local Ethical Committee for Animal Care (University of Nantes, France). Sixteen female New Zealand White (NZW) rabbits, about 4 months old, weighing approximately 3.5 kg, were purchased from a Grimaud (France). The animals were housed in individual cages measuring 75×47×40 cm at the Unit for experimental technology (UET, Nantes). The rabbits were fed daily with granular food (35 g/kg body weight) and water ad libidum. The national guidelines for the care and use of laboratory animals were strictly observed. The materials were implanted in female New Zealand White rabbits for a follow-up time of 4 and 10 weeks.

Surgical Procedure

Eight rabbits were anesthetized by intramuscular injection of Ketamine (rompun 2%) and xylazine (imalgene) (respectively 0.25 mg/kg and 0.35 ml/kg of body weight). The implantation area (calvaria) was shaved and disinfected with iodine (2% in alcohol 50%). A u-shaped incision was made on the calvaria, from each ear backward to the sinus area forward. The skin was lifted to reveal the periosteum that was incised following a similar u-pattern. Four 8 mm bone defects placed as a cross on the calvaria were then performed using a trephine. Special care was taken not to perforate the brain dure mere. The created defects were covered with the different membranes, cut to 1×1 cm squares. The nanofibrillar biomimetic layer of the bilayered membranes faced the brain side of the defect. The four corner of each applied membrane were glued with cyanolite to the defect borders prior to closing back the periosteum with non-resorbable 4/0 sutures. The skin was sutured with 3-0 Vicryl sutures. After surgery, antibiotic medication was injected intramuscularly.

Implants

Four PCL bilayered membranes, four PCL single nanofibrillar biomimetic layers and four PLGA single nanofibrillar biomimetic layers were implanted for each time point (4 and 10 weeks). A commercial dense synthetic membrane composed of poly lactic acid was also included in the study (n is three for each implantation time). Furthermore, two defects were left empty as negative control for each implantation period. Each implant type was never applied twice at the same defect position on the calvaria.

Analysis of Retrieved Implants

The rabbits were sacrificed after 4 and 10 weeks by intra-cardiac injection of pentobarbital, after anesthesia. After retrieval of the calvarias (cut with a saw), the implants and surrounding bone were processed according to standard operating procedures for histology. The blocks were immersed in 10% formaldehyde, dehydrated in a graded series of ethanol and embedded in glycolmethacrylate (MMA). After polymerization, each of four calvaria defects was cut twice longitudinally using a diamond-saw microtome (Leica, Rijswijk) and stained with methylene blue and basic fuchsin. The remaining parts of the cross-sections were polished and gold sputter-coated using a Cressington 108 auto apparatus prior to analysis with a Leo 1450 VP electronic microscope using Back-Scattered Electron (BSE) mode.

Results

Characterisation of Biomimetic GBR Membranes

The synthetic GBR membranes, bi-layered or monolayered and composed of either PCL or PLGA, were easily and swiftly produced by polymer spraying. 10×10 cm squares could be produced within ten minutes. Macroscopically, the membranes surface was homogeneous and smooth (FIGS. 2a and 2b). No delamination between the two layers was observed during handling. The membrane thickness was homogenously distributed and varied from 473±3 μm for bi-layered membranes (including a dense polymer film of 79±1 μm) to 394±3 μm for mono-layer membranes composed of nanofibers. The membranes density was of 12.7 mg/cm$^2$ while nanofibrillar layer porosity was substantially of 95%, i.e. of 94.4±0.4%.

In agreement with the elevated nanofibrillar layers porosity, the entangled fibers resulted in a highly open structure with very good interconnection between pores. The permeability coefficient of the structures (K), calculated from the water conductance of nanofibrillar layers, confirmed a highly permeable structure. K was comprised between $1*10^{-9}$ m$^2$ and $4*10^{-9}$ m$^2$, in particular between 1 m$^2$ and $3.7\times10^{-9}$ m$^2$ with an average value of substantially of $2*10^{-9}$ m$^2$, i.e. $1.98\pm0.78\times10^{-9}$ m$^2$. These values are within the range of human trabecular bone (0.4-11 $10^{-9}$ m$^2$).

Microscopically, the biomimetic layer was composed of entangled nanofibers comprised between 289 and 1282 nm, with an average diameter of 608 nm (FIG. 3b). Conversely, the dense layer of PCL was smooth and uniform (FIG. 3a).

Biological Efficacy of Biomimetic GBR Membranes

The membranes were easy to handle, to cut with scissors and to apply over the bone defects. Possibly due to their nanofibrillar and therefore highly open structure, the implants appeared haemostatic and readily absorbed physiological fluids. As a result, they adhered on the defect border once in position but could nevertheless be removed and re-positioned if necessary. The bi-layered membranes were sufficiently flexible to cover the convex calvaria defects without need for cyanolite fixation. Conversely, the PLA dense commercial membranes were more rigid and needed fixation to fully cover the defects on all borders.

Figure 7A:
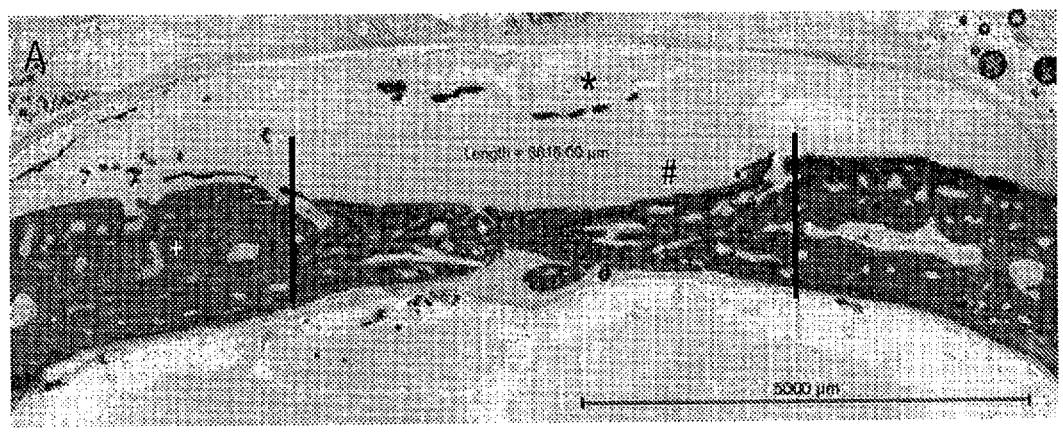
Figure 7B:
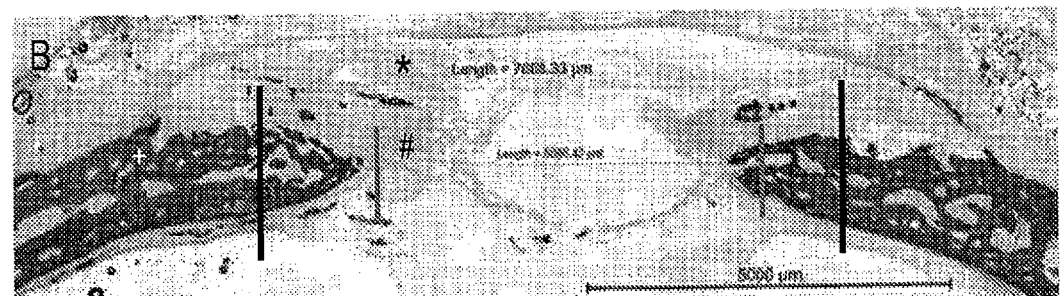

After 4 weeks of implantation, all membranes were well tolerated and no sign of infection was visible. The different implants provided dissimilar levels of bone repair while defects left empty (negative controls) did not show bone formation. As can be seen in FIGS. 7a and 7b where bone is specified with + while * and # respectively indicate the dense and nanofibrillar layers, the defect borders are delimited with black lines and the extent of bone growth with grey lines, bi-layered PCL membranes induced the formation of a thick and mature new bone layer, growing centripetally from the defect border. Newly formed bone bridging the defect was visible on a cross section performed at a third of the defect (FIG. 7a) while a section in the middle (FIG. 7b) showed a lower bone formation.

Figure 8:
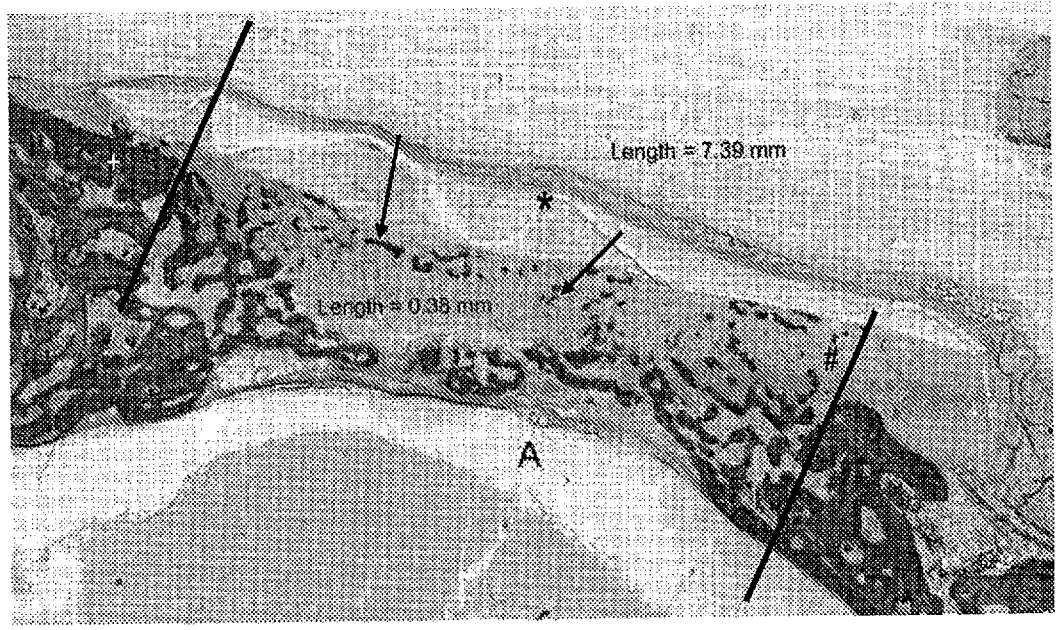
FIG. 8 is a cross-section microscopic view of the middle of a calvaria defect covered for four weeks with the bi-layered membrane of FIG. 1, FIGS. 9a and 9b are cross-section microscopic views of a representative calvaria defect covered for four weeks by a single nanofibrillar membrane.

FIG. 8 is a middle cross section of the calvaria defect covered for four weeks with the membrane. Bone is specified with + while * and # respectively indicate the dense and nanofibrillar layers, the defect borders are delimited with red lines and arrows show bone formation within the nanofibrillar layer. The nanofibrillar layer associated with the dense film appeared well recognized as a biomimetic extracellular matrix for bone precursor and bone cells. Indeed, bone formation was observed within the nanofibrillar network, indicating that cells penetrated in and used the structure as template for the deposition of mineralized matrix.

Figure 9A:
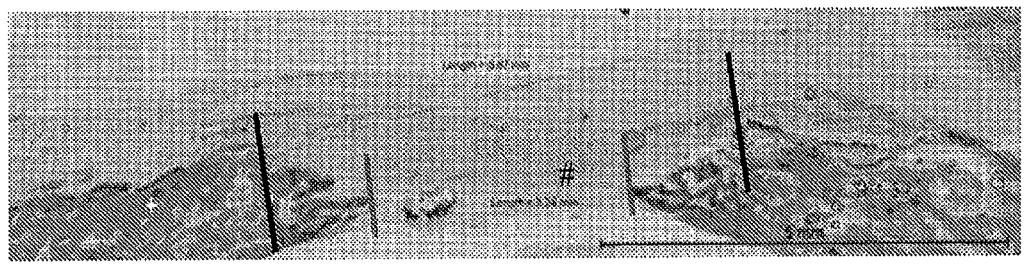
Figure 9B:
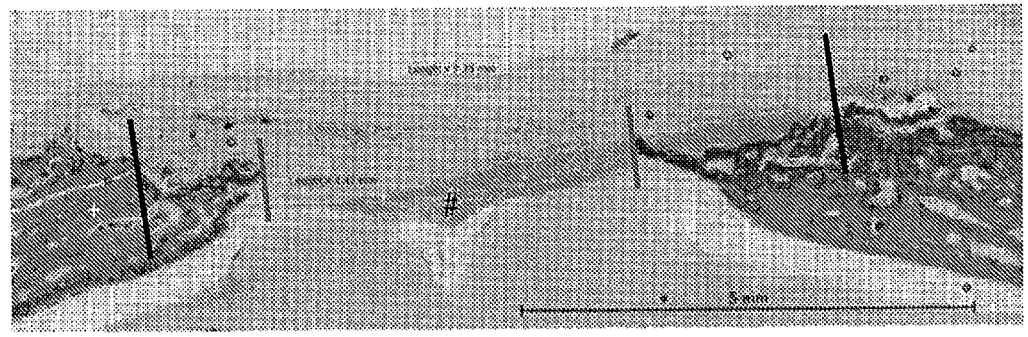

As can be seen on FIGS. 9a and 9b where # indicates the nanofibrillar layer and the defect borders are delimited with black lines and the extent of bone growth with grey lines, the implantation of mono-layered membranes composed a single nanofibrillar layer clearly indicated the importance of the dense polymer layer for bone formation. Without the mechanical support of the dense layer, the nanofibrillar membrane penetrated within the defect space, therefore probably preventing an efficient bone formation. In addition, no bone formation was visible within the nanofibrillar network, which further underlines the beneficial effect of the dense layer. By preventing fibroblastic infiltration from the skin side of the defect within the biomimetic layer, the dense layer allows the colonisation of the nanofibers by osteoblasts and bone precursor cells.

Figure 10A:
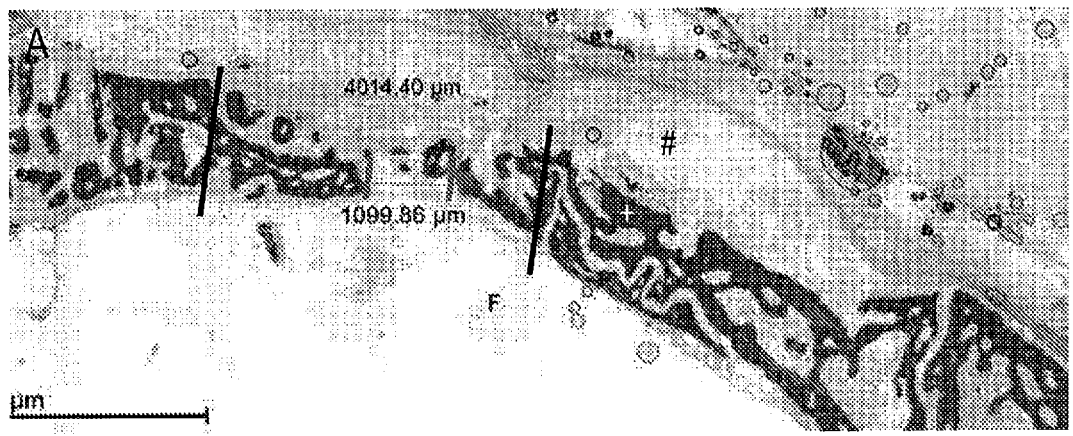
Figure 10B:
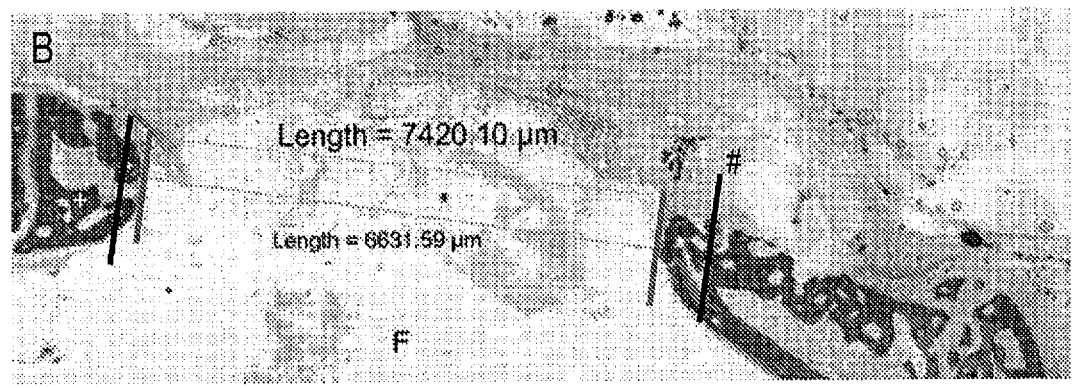

FIGS. 10a and 10b are cross section microscopic views of the calvaria defect covered during four weeks by a commercial PLA dense membrane, taken at the first third of the defect (FIG. 10a) and at the middle of the defect (FIG. 10b). Bone is specified with + while # indicate the PLA membrane. The defect borders are delimited with black lines and the extent of bone growth with grey lines. In comparison to bi-layered membranes, the commercial PLA dense membranes provided a lower level of bone formation. Indeed, cross sections at similar levels of the defect indicated a thinner newly formed bone, without full bridging. Moreover, cross sections in the middle of the defects indicated a lower amount of centripetal bone growth. Although the membrane probably prevented fibroblastic invasion within the defect space, it is likely that the lack of a suitable biomimetic structure supporting bone cell invasion reduced bone formation.

The invention claimed is:

1. A method for forming a bone regeneration membrane, comprising the steps of:

forming, at room temperature, a dense layer made of resorbable polymer, said dense layer having first and second opposite surfaces and being adapted to form a barrier to cells and soft tissues, the step of forming the dense layer comprising the steps of:

mixing the resorbable polymer with a solvent to obtain a polymer solution, casting said polymer solution onto a collecting surface, spreading said polymer solution on the collecting surface, wherein the cast and spread resorbable polymer precipitates and solidifies by evaporation of the solvent to form a substantially non-porous film, forming, at room temperature, a nanofibrillar layer made of resorbable polymer, said nanofibrillar layer comprising fibers having a diameter of nanometer size, the step of forming the nanofibrillar layer comprising the steps of:

mixing the resorbable polymer with a solvent to obtain a polymer solution, feeding a spray nozzle with said polymer solution, projecting said polymer solution through said nozzle with a gas jet adapted to pump the polymer solution by depression, wherein the projected resorbable polymer precipitates and solidifies by evaporation of the solvent to form the fibers interlaced so as to present an average pore size greater than 10 μm to allow cell permeability and bone tissue regeneration, the nanofibrillar layer having a permeability κ between $0.4*10^{-9}$ m$^2$ and $11*10^{-9}$ m$^2$, depositing the fibers on a collecting surface, attaching, at room temperature, said nanofibrillar layer to the first surface of the dense layer, wherein the nanofibrillar layer is deposited on the first surface of the dense layer as collecting surface during the step of spreading the polymer solution, the step of attaching the nanofibrillar layer to the first surface of the dense layer comprising the formation of hydrogen bonds as the polymer of which the dense layer is made precipitates and solidifies by evaporation of the solvent.

2. The method according to claim 1, wherein at the step of projecting the polymer solution, the polymer solution is directly projected onto the first surface of the dense layer, and at the step of depositing the fibers, the fibers are directly deposited on the first surface of the dense layer as collecting surface, the step of attaching the nanofibrillar layer to the first surface of the dense layer comprising the formation of hydrogen bonds as the polymer of which the nanofibrillar layer is made precipitates and solidifies by evaporation of the solvent.

3. The method according to claim 1, wherein the step of forming a nanofibrillar layer further comprises, at the step of projecting the polymer solution, spraying particles adapted to support bone formation.

4. The method according to claim 1, further comprising a step of sterilising the bone regeneration membrane.

5. The method according to claim 1, wherein the nanofibrillar layer has a permeability $\kappa$ between $1*10^{-9}$ m$^2$ and $4*10^{-9}$ m$^2$.

6. The method according to claim 1, wherein the nanofibrillar layer has a permeability $\kappa$ of $2*10^{-9}$ m$^2$.

* * * * *